US006292681B1

(12) United States Patent
Moore

(10) Patent No.: US 6,292,681 B1
(45) Date of Patent: *Sep. 18, 2001

(54) COMBINED MOTOR DRIVE AND AUTOMATED LONGITUDINAL POSITION TRANSLATOR FOR ULTRASONIC IMAGING SYSTEM

(75) Inventor: Thomas C. Moore, Fremont, CA (US)

(73) Assignee: Boston Scientific Corporation, Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/468,288

(22) Filed: Dec. 20, 1999

Related U.S. Application Data

(63) Continuation of application No. 09/074,064, filed on May 7, 1998, now Pat. No. 6,004,271.

(51) Int. Cl.[7] ................... A61B 5/05; A61B 8/12
(52) U.S. Cl. ................ 600/407; 600/445; 600/463; 600/437
(58) Field of Search .................. 600/407, 437, 600/439, 159, 169–171; 604/131, 208–211, 264, 280, 283; 128/DIG. 1

(56) References Cited

U.S. PATENT DOCUMENTS

| 4,679,551 | 7/1987 | Anthony . |
| 4,708,125 | 11/1987 | Miketi et al. . |
| 4,753,248 | 6/1988 | Engler et al. . |
| 4,771,774 | 9/1988 | Simpson et al. . |
| 4,794,931 | 1/1989 | Yock . |
| 4,802,487 | 2/1989 | Martin et al. . |
| 4,815,661 | 3/1989 | Anthony . |
| 4,951,677 | 8/1990 | Crowley et al. . |
| 5,000,185 | 3/1991 | Yock . |
| 5,105,819 | 4/1992 | Wollschlager et al. . |
| 5,107,844 | 4/1992 | Kami et al. ............. 600/446 |
| 5,115,814 | 5/1992 | Griffith et al. . |
| 5,125,410 | 6/1992 | Misono et al. . |
| 5,178,148 | 1/1993 | Lacoste et al. . |
| 5,211,176 | 5/1993 | Ishiguro et al. ........ 600/445 |
| 5,295,486 | 3/1994 | Wollschlager et al. . |
| 5,361,768 | 11/1994 | Webler et al. . |
| 5,383,460 | 1/1995 | Jang et al. ............. 600/463 |
| 5,485,846 | 1/1996 | Webler et al. . |
| 5,497,776 | 3/1996 | Yamazaki et al. ....... 600/446 |
| 5,592,942 | 1/1997 | Webler et al. .......... 600/446 |
| 5,759,153 | 6/1998 | Webler et al. .......... 600/445 |
| 5,827,313 | * 10/1998 | Roam ................... 600/471 |
| 6,004,271 | * 12/1999 | Moore .................. 600/446 |
| 6,013,030 | 1/2000 | Webler et al. . |

FOREIGN PATENT DOCUMENTS

| 0212225 A1 | 3/1987 | (EP) . |
| 021225 B1 | 3/1987 | (EP) . |
| 90/02520 | 3/1990 | (WO) . |
| 90/13259 | 11/1990 | (WO) . |
| 92/03095 | 3/1992 | (WO) . |

* cited by examiner

Primary Examiner—Francis J. Jaworski
(74) Attorney, Agent, or Firm—Lyon & Lyon LLP

(57) ABSTRACT

A vascular imaging system with an automated longitudinal position translator includes a drive unit with a single motor to provide for rotational and longitudinal translation of a drive-cable and distally mounted transducer within a catheter assembly. The drive unit includes a main body casing and a pullback carriage on which the main body casing slidingly engages. The drive-cable is mechanically coupled to the motor, and an outer sheath of the catheter assembly is fixed to the pullback carriage via a rigid pullback arm. The imaging system can be made to operate in an automated longitudinal translation mode, wherein the main body casing of the drive unit is made to uniformly and longitudinally move relative to the pullback carriage by the drive unit motor, thus causing coincident longitudinal movement of the drive-cable (and distally located transducer) relative to the outer guide sheath of the catheter assembly.

18 Claims, 6 Drawing Sheets

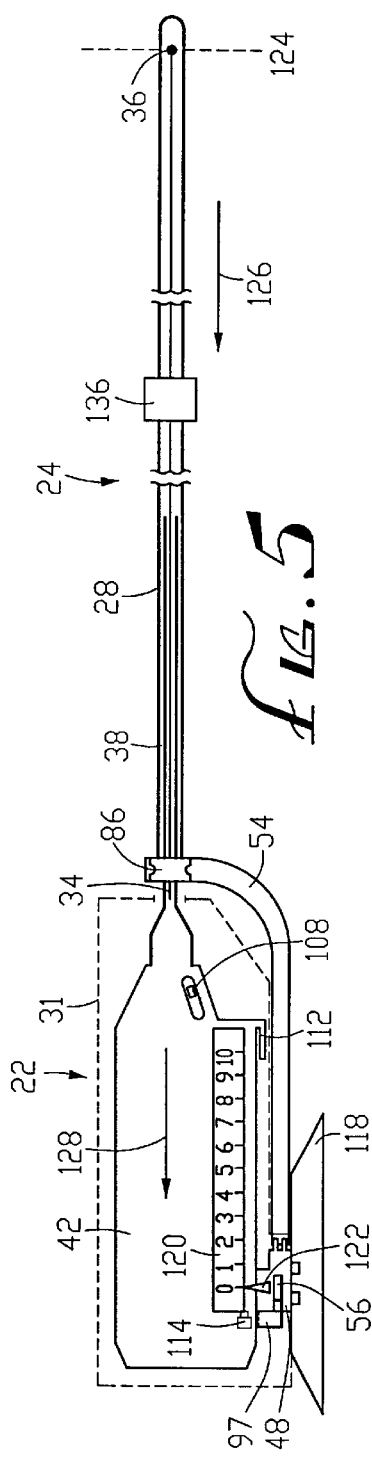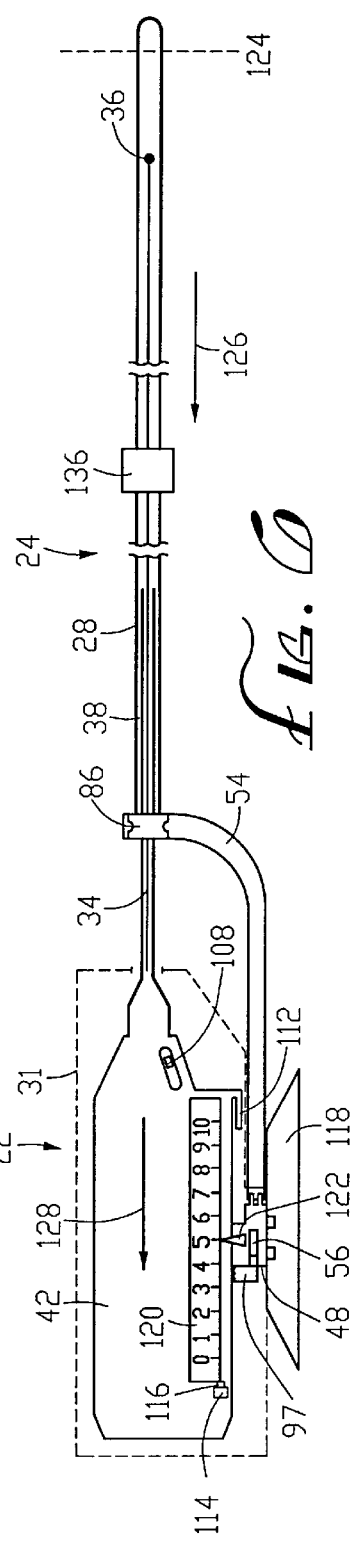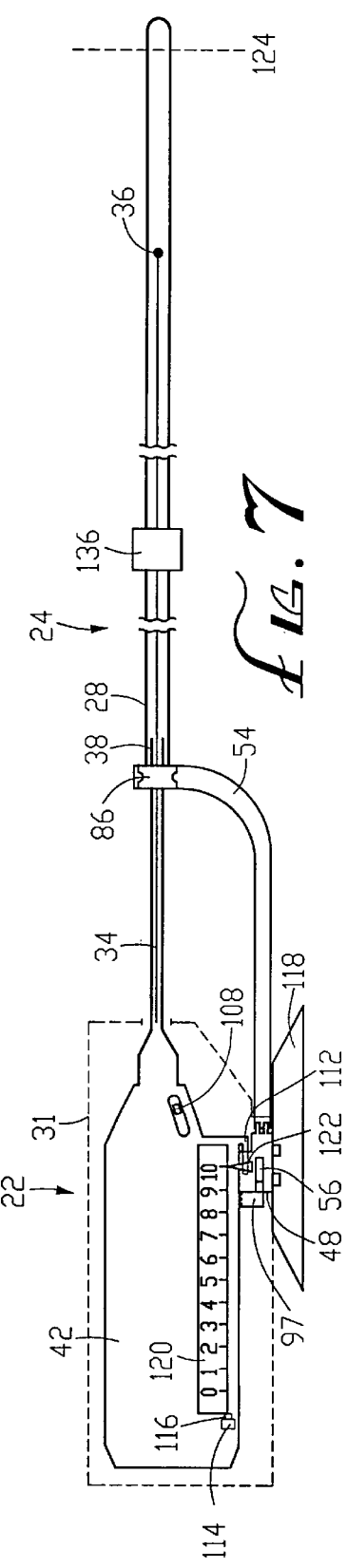

COMBINED MOTOR DRIVE AND AUTOMATED LONGITUDINAL POSITION TRANSLATOR FOR ULTRASONIC IMAGING SYSTEM

CROSS REFERENCE TO RELATED APPLICATIONS

This is a continuation of U.S. application Ser. No. 09/074,064, filed May 7, 1998 now U.S. Pat. No. 6,004,271. The disclosure of the prior application is hereby incorporated by reference in its entirety.

FIELD OF THE INVENTION

The present invention pertains generally to diagnostic and therapeutic ultrasonic imaging systems and, more particularly, to apparatus for providing automated longitudinal position translation in ultrasonic imaging systems.

BACKGROUND OF THE INVENTION

Probe assemblies having therapeutic and/or diagnostic capabilities are being increasingly utilized by the medical community as an aid to treatment and/or diagnosis of intravascular and other organ ailments. In this regard, U.S. Pat. No. 5,115,814 discloses an intravascular ultrasonic imaging assembly with a distally located imaging element that is positionable relative to intravascular sites. Operation of the imaging element in conjunction with associated electronic image recovery components generates visible images that aid an attending physician in his or her treatment of a patient's vascular ailments. In particular, a physician may view in real (or essentially near real) time intravascular images generated by the ultrasonic imaging probe element to locate and identify intravascular abnormalities that may be present and thereby prescribe the appropriate treatment and/or therapy.

The need to accurately position a distally located operative imaging element relative to an intravascular site using any therapeutic and/or diagnostic probe assembly is important so that the attending physician can confidently determine the location of any abnormalities within the patient's intravascular system. Accurate intravascular position information for the imaging assembly will also enable the physician to later replicate the same positions for subsequent therapeutic and/or diagnostic procedures, e.g., to enable the physician to administer a prescribed treatment regimen over time and/or to later monitor the effects of earlier therapeutic procedures.

By using computer-assisted reconstruction algorithms, current ultrasonic imaging systems enable physicians to view a representation of the patient's interior intravascular structures in both two and three dimensions (i.e., so-called three dimensional or longitudinal view reconstruction). To this end, image reconstruction algorithms employ data-averaging techniques which assume the intravascular structure between an adjacent pair of data samples is an average of each such data sample, i.e., the algorithms use graphical "fill in" techniques to depict a selected section of a patient's vascular system under investigation. Of course, if data samples are not sufficiently closely spaced, lesions and/or other vessel abnormalities may go undetected, since they might lie between a pair of data samples and thereby be "masked" by the image reconstruction algorithms.

As such, current reconstruction algorithms depend upon the ability to obtain and process very precisely longitudinally separated data samples of a section of a patient's vascular system under investigation. To this end, automated longitudinal translation of a distally located ultrasound imaging element is often employed to ensure the data samples are precisely spaced. For example, U.S. Pat. No. 5,485,486 discloses an imaging system in which an ultrasound imaging transducer is mounted on a distal tip of a rotating cable extending through a lumen of a catheter placed in a patient's vascular system, wherein the distal tip of the rotating cable is translated longitudinally at a precise constant rate through the use of a longitudinal translation assembly. In particular, the longitudinal translation assembly enables a series of precisely separated data samples to be obtained thereby minimizing (if not eliminating) distorted and/or inaccurate reconstructions of the ultrasonically scanned vessel section, i.e., since a greater number of more closely spaced data samples can reliably be obtained. Further, a precisely controlled pullback speed makes it possible to take measurements in a longitudinal direction, e.g., a lesion length.

Notably, a main advantage of this automated pullback assembly is that it can be operated in a "hands-off" manner which allows the physician to devote his or her attention entirely to the real-time images with the assurance that all sections of the vessel are displayed. On the other hand, the disclosed system is relatively large and can be cumbersome for a physician to set up, in part because the longitudinal translation assembly and a rotary drive motor used to rotate the imaging cable must each be wrapped in separate sterile drapes (i.e., plastic bags) in order to perform the imaging procedure.

U.S. Pat. No. 5,361,768 discloses an improved system over that disclosed in U.S. Pat. No. 5,485,486, in that a single drive unit provides the requisite longitudinal and rotational translation of the imaging cable. However, the respective rotational and longitudinal movement of the cable is still provided by separate motors, thereby making the "combined" drive unit larger and heavier than either of the previous separate units.

Thus, it remains desirable to provide a still further improved drive unit for both rotational and precisely controlled translational movement of an imaging cable in an ultrasonic catheter imaging system.

SUMMARY OF THE INVENTION

The present invention is directed to an ultrasonic imaging system employing a single motor drive unit for providing both rotational and controlled longitudinal translation of an operative imaging cable disposed in a catheter assembly, thereby reducing the size, weight and cost of the system drive unit(s), while at the same time making the imaging system easier to set up and operate.

In a preferred embodiment, the imaging system includes an imaging catheter assembly secured to a single motor drive unit, wherein the imaging catheter assembly generally comprises an outer guide sheath having an operative drive-cable and mounted transducer disposed therein. The motor drive unit includes a main body casing that houses a motor that rotates a drive-shaft at a specific and predetermined rotational drive-shaft speed.

The main body casing includes one or more guide rails that are slidingly mounted on a pullback carriage, such that the main body casing may move longitudinally relative to the pullback carriage. A rigid "pullback arm" is connected at one end to the pullback carriage and at the other end to the proximal opening of the outer guide sheath of the catheter assembly, i.e., such that the main body casing is also movable relative to the outer guide sheath of the catheter assembly as the pullback carriage slides along the guide rail(s). A telescoping inner catheter sheath extends through the fixed proximal opening of the outer guide sheath and is attached to the main body casing of the motor drive unit, with the drive-cable extending through the inner sheath and attached to the motor drive-shaft within the hub, i.e., such that rotation of the motor drive-shaft correspondingly rotates the drive-cable.

In accordance with a first aspect of the invention, the imaging system can be made to operate in an automated longitudinal translation mode, wherein the main body casing of the drive unit is made to uniformly and longitudinally move relative to the pullback carriage by the drive unit motor, thus causing coincident longitudinal movement of the drive-cable (and distally located transducer) relative to the outer guide sheath of the catheter assembly.

In particular, a reduction gear mechanism is mounted circumferentially around the drive-shaft within the main body casing of the drive unit, with the reduction gear mechanism producing an output circumferential speed that is significantly less than the circumferential speed of the drive-shaft. A longitudinal drive train, such as, e.g., a drive screw and threaded collar, is rotatably mounted to the main body casing of the drive unit, engaging the reduction gear mechanism. In order to provide longitudinal movement of the main body casing relative to the pullback carriage, (i.e., while the later is in a fixed, or mounted position), an engagement mechanism associated with the pullback carriage and urged by an expansion spring is caused to engage the threads of the drive screw. Notably, because the circumferential speed of the drive screw is much less than, but linearly proportional to the circumferential speed of the drive-shaft, the main body casing moves relative to the pullback carriage at a rate that is linearly proportional to the motor drive-shaft speed.

In accordance with a further aspect of the invention, a mechanical disengagement member may be provided integral with a distal portion of the main body casing of the motor drive unit, which acts as a limit switch to prevent further longitudinal movement of the main body casing relative to the pullback carriage. In particular, the mechanical disengagement member is preferably provided in a position relative to the engagement mechanism such that as the main body casing reaches its most "proximal" position relative to the pullback carriage (i.e., farthest from the distal end of the main guide sheath of the catheter assembly, the mechanical disengagement member makes contact with the engagement mechanism, thereby disengaging the engagement mechanism from the drive screw to prevent further longitudinal translation of the main body casing relative to the pullback carriage.

In accordance with a still further aspect of the invention, a depressible start indicator button may be provided on the main body casing such that the body of the pullback carriage mechanically depresses the start indicator when the main body casing of the drive unit is at its most "distal" position relative to the pullback carriage. As the main body casing automatically and longitudinally moves proximally relative to the pullback carriage, the pullback carriage moves away from (i.e., "releases") the start indicator button, causing a signal to be transmitted to a controller that the automated longitudinal translation mode has commenced.

In accordance with a still further aspect of the invention, a selective latch may be provided that is operatively associated with the engagement mechanism, and which allows the motor drive unit to be selectively operated in or out of the automated longitudinal translation mode. By way of example, in a preferred embodiment, the latch comprises an engagement tab and a ball detent mechanism. In particular, when the engagement tab is moved away from the main body casing, the engagement mechanism and the drive screw are engaged, with the expansion spring maintaining the drive unit in an automated longitudinal translation mode. Conversely, when the engagement tab is moved toward the main body casing of the drive unit, the engagement mechanism and the drive screw are disengaged, with the ball detent mechanism maintaining the drive unit out of an automated longitudinal translation mode.

In accordance with a still further aspect of the invention, a disposable base plate may be removably mounted to the pullback carriage, allowing for the motor drive unit to be stably placed on a support structure such as a table. In a preferred embodiment, the cross-section of the base plate is preferably U-shaped for easy adaptation to the patient's leg.

Other and further objects, features, aspects, and advantages of the present invention will become better understood with the following detailed description of the preferred embodiments illustrated in the accompanying drawings.

BRIEF DESCRIPTION OF THE ACCOMPANYING DRAWINGS

The drawings illustrate both the design and utility of preferred embodiments of the present invention, in which.

Figure 1:
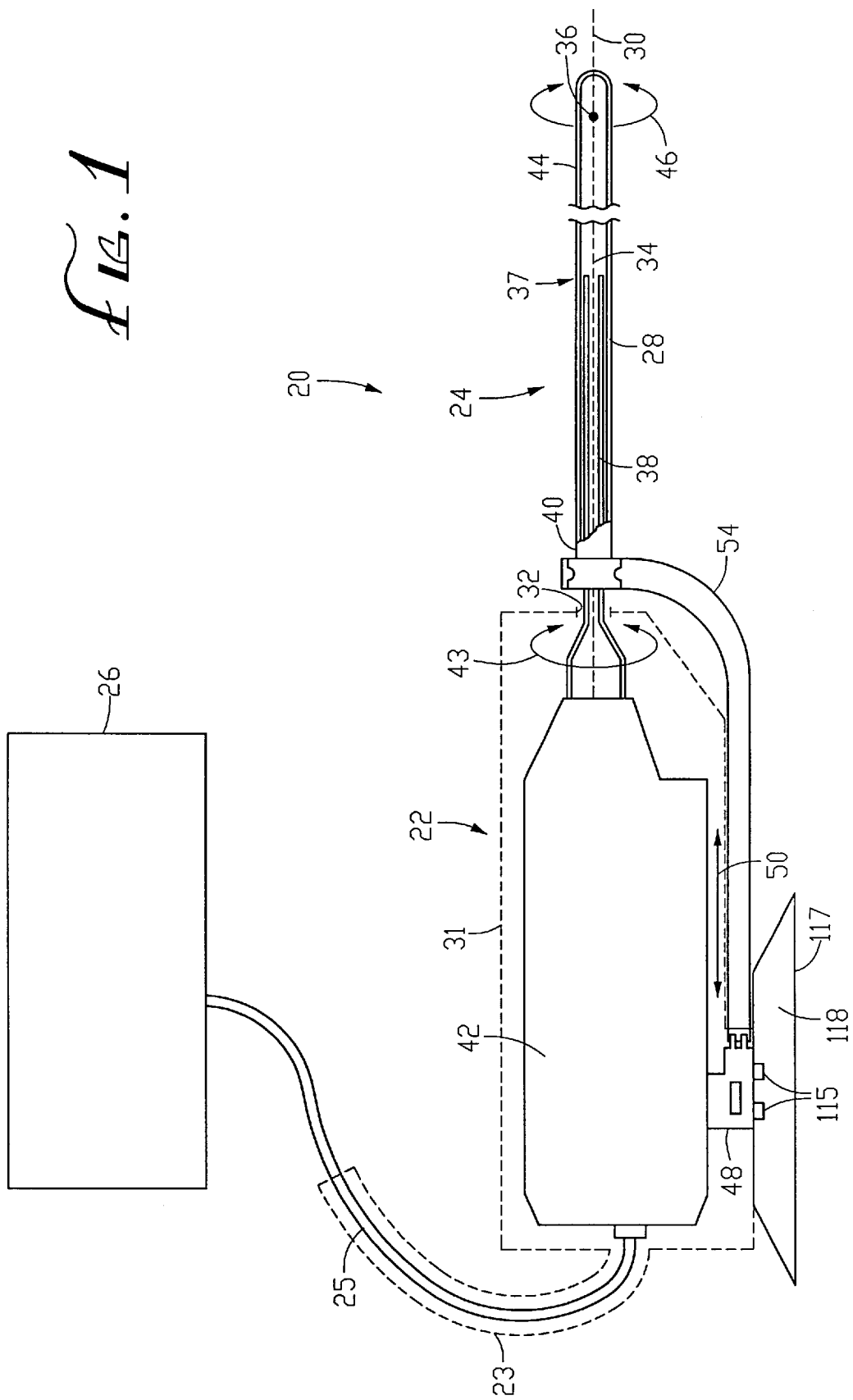
FIG. 1 is a schematic view of a vascular ultrasonic imaging system according to the present invention.
Figure 8:
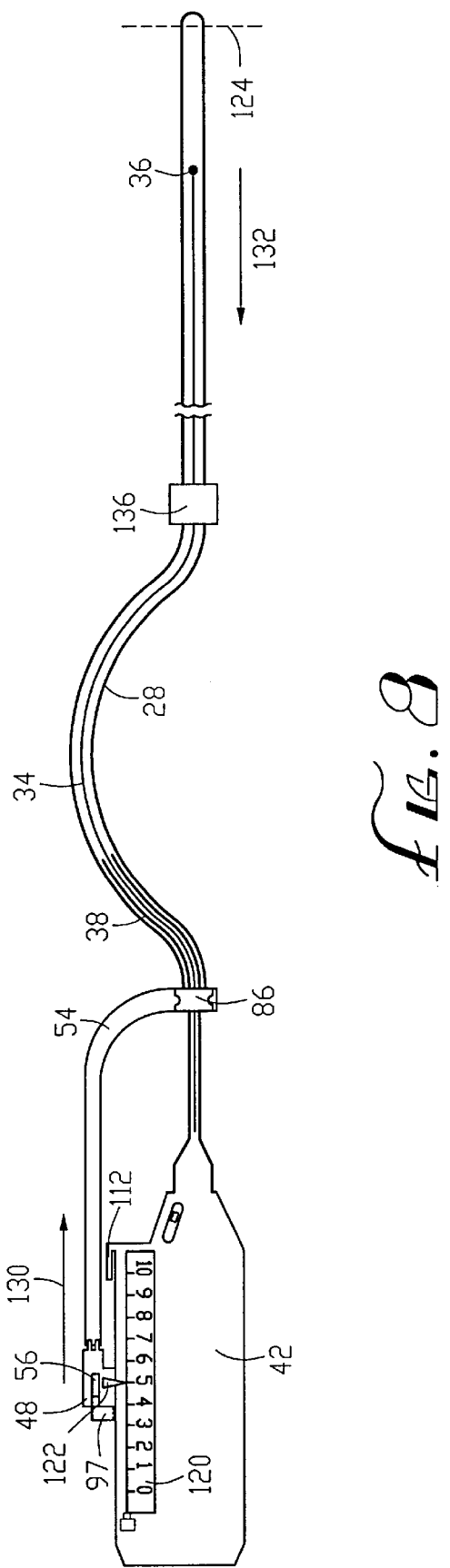

FIG. 4-A is a plan view of an engagement mechanism and ball detent mechanism employed in the vascular ultrasonic imaging system of FIG. 1;

FIG. 4-B is a side view of the engagement mechanism and ball detent mechanism of FIG. 4-A, shown in an engaged position;

FIG. 4-C is a side view of the engagement mechanism and the ball detent mechanism of FIG. 4-A, shown in a disengaged position;

FIG. 5 is a partial side view of the vascular ultrasonic imaging system of FIG. 1, prior to initiation of an automated ultrasonic imaging scan;

FIG. 6 is a partial side view of the vascular ultrasonic imaging system of FIG. 1, during an automated ultrasonic imaging scan;

FIG. 7 is a partial side view of the vascular ultrasonic imaging system of FIG. 1, after termination of an automated ultrasonic imaging scan; and FIG. 8 is a partial side view of the vascular ultrasonic imaging system of FIG. 1, illustrating an alternate method of performing an automated ultrasonic imaging scan.

DETAILED DESCRIPTION OF THE PREFERRED EMBODIMENTS

Referring to FIG. 1, an exemplary ultrasonic imaging system 20 generally comprises a flexible imaging catheter assembly 24 connected to a single motor drive unit 22, with the motor drive unit 22 in electrical communication with an imaging reconstruction console 26 via a power/data communications cable 25. The image reconstruction console 26 generally comprises a controller, data interpretation unit, monitor, keyboard, etc. (not individually shown), wherein the power/data cable 25 transmits input/output data to and from the motor drive unit 22, and also provides DC electrical power.

In accordance with constructions well-known in the art, the catheter assembly 24 generally includes a hollow, outer sheath 28, which defines a longitudinal axis 30 along its axial center. A rotatable drive-cable 34 extends through the outer sheath 28 and has an ultrasonic transducer 36 mounted at its distal end. In a manner described in greater detail below, a reduced diameter, telescoping inner catheter sheath 38 extends from a relatively proximal position (designated by arrow 37) within the outer sheath 28, through a proximal end 40 of the outer sheath 28, and is attached to the motor drive unit 22. The drive-cable 34 extends through the inner sheath 38 and is engaged to a motor drive-shaft 64 (shown in FIG. 2) within the motor drive unit 22.

Notably, the overall length of the catheter assembly 24 is selected for the desired diagnostic and/or therapeutic intravascular procedure. For example, the overall length of the catheter assembly 24 may be relatively shorter for direct (e.g., arteriotomy) insertions as compared to the length needed for percutaneous distal insertions (e.g., via the femoral artery). For ease in illustration, however, only the very proximal (i.e., adjacent the motor drive unit 22) and distal (i.e., at the far tip) portions of the catheter assembly are shown in FIG. 1. By way of non-limiting examples, exemplary preferred imaging catheter assembly constructions in accordance with the general description provided herein may be found in U.S. Pat. Nos. 5,000,185, 5,115,814, 5,464,016, 5,421,338, 5,314,408 and 4,951,677, each of which is fully incorporated herein by reference.

The motor drive unit 22 broadly includes a main body casing 42, a pullback carriage 48, and a rigid pullback arm 54. The main body casing 42 houses the electromechanical elements that cause the drive-shaft 34 to rotate about the longitudinal axis 30, as indicated by arrows 43 and 46. As disclosed and described below, the main body casing 42 is slidingly mounted to the pullback carriage 48, such that the main body casing 42 can be reciprocally and longitudinally moved relative to the pullback carriage 48, as indicated by arrow 50. The pullback arm 54 fixes the proximal end 40 of the outer sheath 28 relative to the pullback carriage 48, with the inner sheath 38 and drive-shaft 34 extending therethrough and fixedly attached to the main body casing 42. In this manner, as the main body casing 42 reciprocally and longitudinally moves relative to the pullback carriage 48, the respective telescoping inner sheath 38 and drive-cable 34 correspondingly move longitudinally relative to the outer sheath 28.

As will be appreciated by those skilled in the art in view of the disclosure herein, the telescoping inner sheath 38 must be of a sufficient length to accommodate the entire "pullback range" of movement of the main body casing 42 relative to the pullback carriage 48, without emerging from the proximal end 40 of the outer sheath 28.

The motor drive unit 22 is also provided with an (optional) base plate 118 that is removably mounted to the pullback carriage 48, e.g., by a plurality of protrusions 115 in the pullback carriage 48 that mate with corresponding openings (not shown) in the base plate 118. Preferably, a bottom surface 117 of the base plate 118 is suitably configured such that the motor drive unit 22 will be stably supported on a flat structure (e.g., such as an operating table), while the imaging system 20 is in operation. Preferably, the cross-section of the base plate 118 (shown in FIG. 3) is "U-shaped" to permit the motor drive unit 22 to be supported on a patient's leg. Notably, the motor drive unit 22 will preferably be compact and light enough to allow a physician to hold the motor drive unit 22 in his or her hand while performing an imaging procedure and the base plate 118 need not necessarily be mounted to the pullback carriage 48.

In presently anticipated preferred embodiments, the pullback arm 54 and base plate 118 will be disposable and supplied in sterile packaging separate from the main body casing 42. Thus, to ensure sterility of all of the components, a relatively thin sterile plastic bag 31 is placed over the main body casing 42 and pullback carriage 48 prior to use. An opening 32 formed at one end of the sterile bag 31 to allow for the catheter assembly 24 to be connected therethrough to the main body casing 42. The sterile bag 31 is also provided with a tubular portion 23 at an opposite end of the main body casing 42 to maintain sterility of the power/data cable 25. The back end portion 23 of the sterile bag 31 preferably extends at least three feet along the power/data cable 25 to prevent the cable 25 from violating the sterile field. Notably, the base plate 118 can preferably be snapped onto the base of the pullback carriage 48 through the relatively thin sterile bag 31, without violating the sterile field.

As will be apparent to those skilled in the art, an advantage of the present invention is that, unlike the prior art in which separate sterile drapes need to be used for each of the rotary drive unit and the longitudinal drive unit, only a single sterile drape needs to be used in conjunction with operation of the motor drive unit 22.

Figure 2:
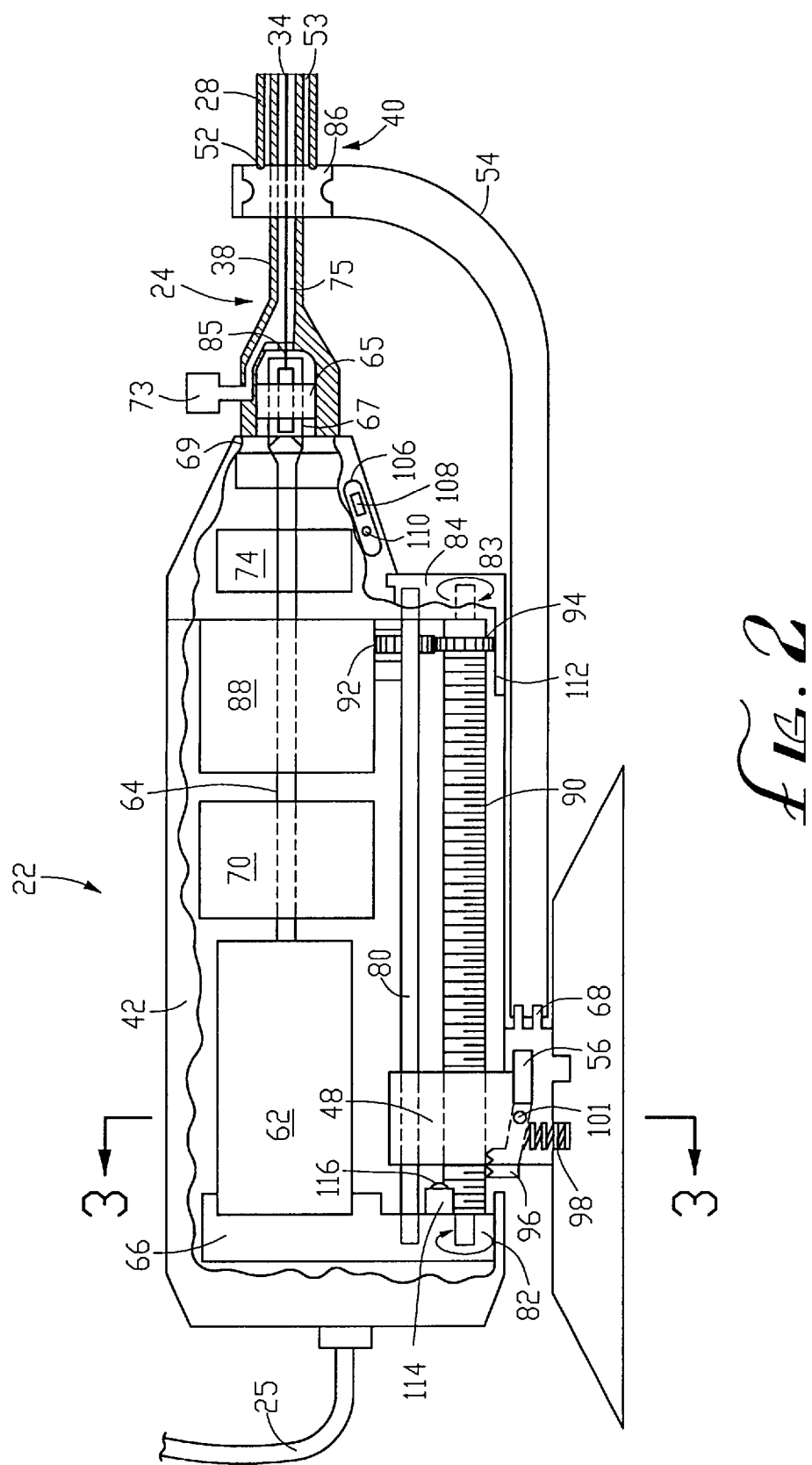
FIG. 2 is a cut-away, partial side view of a drive unit employed with the vascular ultrasonic imaging system of FIG. 1.

Referring to FIG. 2, a drive motor 62, such as a DC brushless motor, is fixably supported within the proximal end of the main body casing 42 of the motor drive unit 22 by a motor support bracket 66. The motor support bracket 66 is attached at the proximal end of the main body casing 42 by suitable means, e.g., such as screws or bonding material (not shown). The drive-cable 34 is mechanically and rotationally coupled to the drive motor 62 through a rigid drive-shaft 64 that extends through the main body casing 42. The drive-shaft 64 is connected at its proximal end to the drive motor 62, and at its distal end 44 to a motor drive-catheter interface 67, which is itself connected to the proximal end of the drive-cable 34.

More particularly, the proximal end 40 of the outer guide sheath 28 is bonded to a cylindrically concave clamping collar 86 having an axial aperture through which the telescoping inner sheath 38 extends. A distal end of the rigid pullback arm 54 is adapted to attach to the clamping collar 86 to provide a secure, non-slip connection between the pullback arm 54 and the outer guide sheath 28, without collapsing the outer guide sheath 28. The proximal end of the pullback arm 54 is adapted to be removably attached to the pullback carriage 48 by a snap (or "clip") connection 68. In this manner, the outer guide sheath 28 may be secured to the pullback carriage 48, such that the main body casing 42 and, thus, the respective inner telescoping sheath 38 and drive-cable 34 are longitudinally movable relative to the proximal end 40 of the outer guide sheath 28.

In a manner well-known in the art, the proximal portion of the inner sheath 38 is formed into an expanded cylindrical shape, including a concave clamping collar 69 that is adapted for attachment to the main body casing 42 of the motor drive unit 22. A fluid flush port 73 is provided to access the lumen 75 formed by the inner sheath 38, wherein the fluid thereby accesses the entire inner lumen area of the catheter assembly 24, i.e., throughout the lumen 53 formed by the outer guide sheath 28 and surrounding the transducer 36 at the distal end thereof. In order to prevent leakage, which can be problematic due to the relative high fluid pressures employed during an imaging procedure, a first fluid seal 52 is placed at the bond connection between the outer guide sheath 28 and pullback arm clamping collar 86, and a second fluid seal 85 is placed around the proximal end of the drive-cable 34, i.e., adjacent the motor drive-catheter interface 67.

As will be appreciated by those skilled in the art, the motor drive-catheter interface 67 is axially disposed within a stationary ring-bearing 65 and makes both electrical and mechanical connections with the drive-shaft 64. In a presently preferred embodiment, the electrical connection comprises a coaxial connection between a first coaxial cable (not shown) extending through the drive-cable 34 (i.e., from the transducer 36 to the motor drive-catheter interface 67) and a second coaxial cable (also not shown) in the drive-shaft 64. Within the motor drive unit 22, a rotary coupler 74 is disposed about the distal end of the drive-shaft 64 and fixably mounted to the main body casing 42. In particular, the rotary coupler 74 includes a rotator element (not shown) disposed in the drive-shaft 64 and electrically coupled to the coaxial cable, in inductive communication with a stationary stator element (also not shown), wherein the stator element is electrically coupled to signal generation and processing circuitry (not shown).

As will be appreciated by those skilled in the art, the rotary coupler 74 may alternately be located within the proximal portion of the catheter assembly body 24, (i.e., such that the motor drive-catheter interface 67 is merely a mechanical interface, and not an electrical interface), which is a technique currently employed in most commercially available imaging catheter systems.

An optical encoder 70 is also disposed around the drive-shaft 64 and fixably mounted to the main body casing 42, and provides rotational speed feedback data to the console controller 26 to control the drive motor 62. Alternately, a DC voltage from a servo affixed to the motor could be used to control the motor speed. Alternately, the drive motor 62 may be a stepper motor, so that the console controller 26 can operate the motor 62 via the power/data cable 25 at an exact and predetermined rotational speed, without requiring the optical encoder 70.

Figure 3:
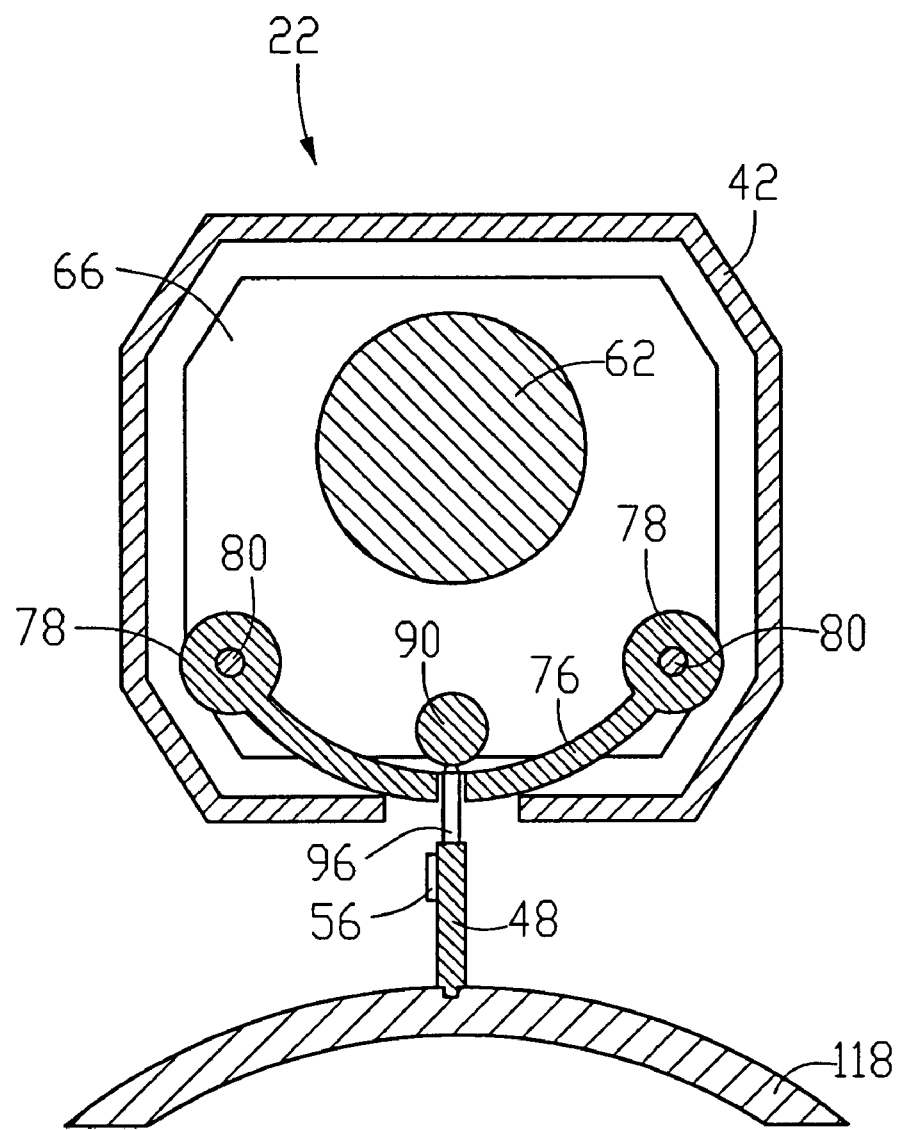
FIG. 3 is a cross-sectional view taken along lines 3—3 in FIG. 2.

Referring to FIG. 3 in addition to FIG. 2, the pullback carriage 48 has a yoke-shaped portion 76 that forms a pair of opposing collars 78, each of which slidingly engages a respective slide rail 80 extending through the main body casing 42. In particular, the respective slide rails 80 are each rigidly fixed at one end to the motor support bracket 66 and at the other end to a support flange 84, which itself is mounted to a distal end of the main body casing 42. In this manner, the main body casing 42 is "slidably mounted" to the pullback carriage 48.

In accordance with a more particular aspect of the invention, the drive motor 62 is operatively coupled to the pull back carriage 48 through a reduction gear mechanism 88 and drive screw 90, respectively. In particular, the reduction gear mechanism 88 is disposed about the drive-shaft 64 and fixably mounted to the main body casing 42 so that, as the drive-shaft 64 rotates, a coupling gear 92 of the reduction gear mechanism 88 rotates in the same axial orientation with a circumferential speed that is significantly less than the circumferential speed of the rotating drive-shaft 64.

The drive screw 90 is rotatably mounted at one end to the motor support flange 66, and at the other to the distal end support flange 84, as indicated by the respective arrows 82 and 83. The drive screw 90 has a circumferentially disposed drive gear 94 that is engaged with the coupling gear 92 of the reduction gear mechanism 88 such that, upon rotation of the drive-shaft 64, the drive screw 90 rotates in the same axial orientation at a circumferential speed that is much less than, but linearly proportional to, the circumferential speed of the drive-shaft 64. Notably, any number of gear sizes and ratios may be employed between the coupling gear and the drive gear, depending on design choice.

Figure 4A:
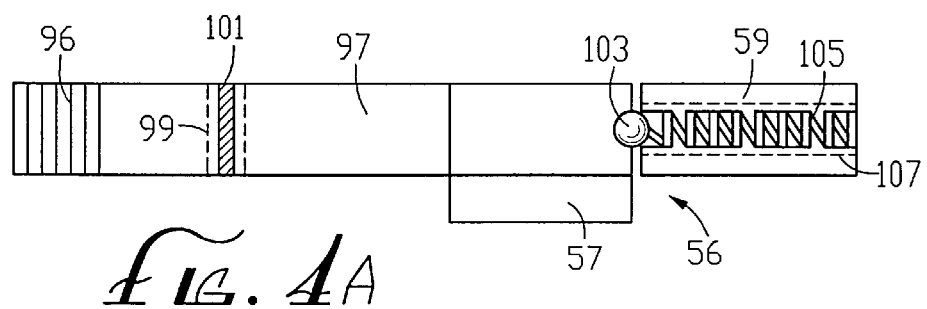
Figure 4B:
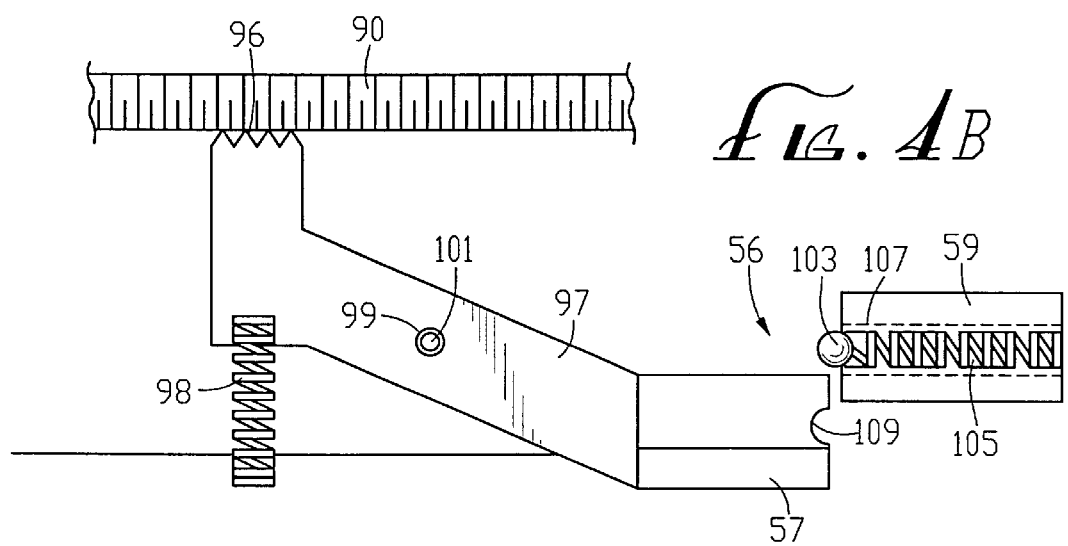
Figure 4C:
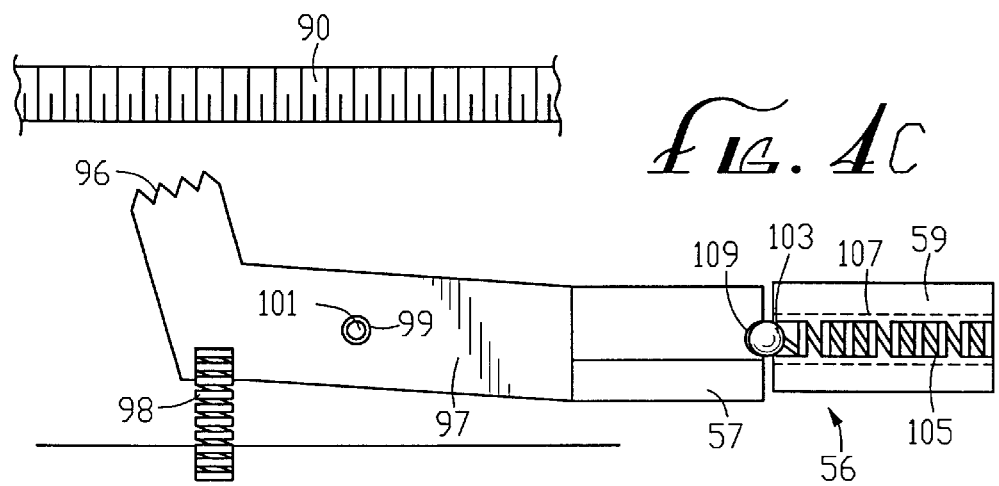

Referring additionally to FIGS. 4A–C, the pullback carriage 48 includes a widthwise axial opening 99 housing a cylindrical pin 101 about which an engagement mechanism 97 having a threaded end 96 (e.g., a threaded collar or the like) is rotatably mounted, i.e., such that the engagement mechanism 97 may pivot about the pin 101. An expansion spring 98 contained within the pullback carriage 48 is positioned in a manner that urges the threaded end 96 of the engagement mechanism 97 to engage the threads of the drive screw 90. When so-engaged, rotation of the drive screw 90 about its longitudinal axis will translate into a controlled and uniform longitudinal displacement of the main body casing 42 relative to the pullback carriage 48, (i.e., during operation of the drive motor 62), thereby resulting in a coincidental translation of the drive-cable 34 relative to the outer guide sheath 28.

Engagement of the threaded end 96 of the engagement mechanism 97 with the threads of the drive screw 90 is controlled by a latch mechanism 56, which allows the imaging system 20 to be selectively operated in an "automated longitudinal translation mode." The latch mechanism 56 includes an engagement tab 57 and a ball detent mechanism 59, which alternately provide for engagement and disengagement of the engagement mechanism 97 and drive screw 90.

The engagement tab 57 is attached to, and preferably integral with, the engagement mechanism 97, wherein movement of the engagement tab 57 toward or away from the main body casing 42 will cause the engagement mechanism 97 to reciprocally rotate about the pin 101, with its threaded end 96 alternately engaging and disengaging the drive screw 90. The ball detent mechanism 59 is attached to, and preferably integral with, the pullback carriage 48, and includes a ball 103 that is partially urged out of an opening 107 by a spring 105. The ball detent mechanism 59 is positioned such that the ball 103 will alternately engage a recess 109 formed in a distal end of the engagement mechanism 97 when the engagement tab 57 is moved toward the main body casing 42 (i.e., from the position shown in FIG. 4-B to the position shown in FIG. 4-C).

In particular, the engagement between the ball 103 and the recess 109 creates a countervailing torque to that created by the expansion spring 98 on the engagement mechanism 97 about pin 101. In this manner, the threaded end 96 of the engagement mechanism 97 and the drive screw 90 are maintained in a disengaged position, absent the continued application of external force on the engagement tab 57. Contrariwise, as the engagement tab 57 is moved away from the main body casing 42 (i.e., from the position shown in FIG. 4-C to the position shown in FIG. 4-B), the recess 109 is forced to disengage the ball 103, and thus the engagement mechanism 97 and the drive screw 90 become engaged. The expansion spring 98 exerts enough force on the engagement mechanism 97 to maintain an engaged position with the drive screw 90, absent the continued application of external force on the engagement tab 57.

As will be appreciated by those skilled in the art, the respective threads of the drive screw 90 and engagement mechanism 97, as well as the rotation orientation of the drive screw 90, are selected so as to effect relative longitudinal shifting of the pullback carriage 48 from the distal end of the drive screw 90 toward the proximal end thereof, i.e., relative to the catheter assembly 24). However, these parameters could be changed so as to effect a reverse (i.e., proximal to distal) relative displacement of the pullback carriage 48, if desired.

Preferably, the reduction ratio of the reduction gear mechanism 88 is relatively high, e.g., 100:1, so that the circumferential speed of the drive screw 90 rotating about its longitudinal axis is much slower than that of the drive-shaft 64, thereby resulting in a slow and controlled longitudinal movement of the drive-cable 34 (e.g., about 1 mm/second). Of course, other longitudinal translation rates may be provided by varying the output parameters of the drive motor 62, reduction gear mechanism 88, drive screw 90, coupling gear 92, and/or drive gear 94.

Notably, using a reduction gear mechanism 88 with such a high reduction gear ratio allows for a minimal amount of power is used to rotate the drive screw 90 about its longitudinal axis. As a result, the size of the drive motor 62 can be minimized and need not be any larger than that typically used to rotate a drive-cable. Further, in alternate preferred embodiments, the reduction gear mechanism 88 may be provided with multiple switchable reduction ratios to allow the imaging system 20 to alternately operate with varying longitudinal translation speeds during an automated longitudinal translation mode.

The imaging procedure (either in or out of the automated longitudinal translation mode) can be conveniently commenced or terminated through the use of a thumb/finger start switch 108 mounted in an opening 106 of the distal end of the main body casing 42, and electrically coupled to selectively actuate the drive motor 62. An LED 110, which indicates the commencement of an imaging procedure, is also mounted in the opening 106, wherein the start switch 108 and LED 110 are positioned such that they each pass only a short distance through the opening 106. Alternately, it may be desirable to prevent inadvertent movement of the switch 108, (e.g., to prevent inadvertent actuation of the motor drive 62), in which case the switch 108 should be sized and located such that it is accessible without extending through the opening 106.

A proximally extending mechanical disengage member 112, which is preferably integral with the support flange 84, acts as a limit switch to prevent the drive gear 94 of the drive screw 90 from making contact with the distal face of the pullback carriage 48 during the automated longitudinal translation mode. In particular, as the distal face of the pullback carriage 48 "approaches" the drive gear 94, the mechanical disengage member 112 "approaches" the engagement mechanism 97. The length of the disengage member 112 is preferably selected such that, immediately prior to the drive gear 94 making contact with the distal face of the pullback carriage 48, the proximal end of the mechanical disengage member 112 makes contact with, thereby rotating the engagement mechanism 97 about pin 101 in a manner that disengages the threaded end 96 of the engagement mechanism 97 from the drive screw 90. This movement will also cause the ball 103 to engage the recess 109, thereby locking the engagement mechanism 97 away from the drive screw 90.

An electric start indicator 114 is mounted to the drive motor support flange 66, and is electrically coupled to the console controller 26 via the power/data cable 25 to indicate the commencement of the automated longitudinal translation mode. In particular, prior to commencement of the automated longitudinal translation mode, an actuating button 116 mounted on the start indicator 114 is depressed by the proximal face of the pullback carriage 48, as the later is placed in a starting position relative to the main body casing 42. When the automated longitudinal translation mode is commenced, the pullback carriage 48 moves away from, thereby releasing the button 116 and causing a corresponding signal to be sent from the start indicator 114 to the console controller 26.

As will be appreciated from the present disclosure by those skilled in the art, if desired, a similar mechanically actuated switch could be provided at the distal end of the main body casing (i.e., attached to the front support bracket 84) to indicate that a pullback procedure is complete.

As depicted on FIG. 5, the motor drive unit 22 preferably includes a scale 120 mounted on the outside of the main body casing 42. A pointer 122 attached to, and preferably integral with, the pullback carriage 48 is positionally associated with the scale 120 to provide information regarding the longitudinal movement of the transducer 36 between respective starting and ending positions within the outer guide sheath during a pullback procedure, i.e., longitudinal movement of the main body casing 42 relative to the pullback carriage 48 over an incremental distance will effect a corresponding movement of the transducer 36 relative to its most distal position within the outer guide sheath 28 by that same incremental distance.

With reference to FIGS. 5–8, operation and use of the imaging system 20 is now described. The motor drive unit 22 is initially manually placed in its "starting" position, i.e., the main body casing 42 is placed at its most distal position relative to the pullback carriage 48—so that the proximal face of the pullback carriage 48 depresses the actuator button 116 on the start indicator 114. The physician or other hospital personnel can perform this step by sliding the engagement tab 56 toward the main body casing 42, so that the engagement mechanism 97 is disengaged from the drive screw 90. The pullback carriage 48 can then be moved proximally while grasping the main body casing 42. To prevent inadvertent movement from the starting position, the motor drive unit 22 should be locked into position by sliding the engagement tab 56 away from the main body casing 42 such that the threaded end 96 of the engagement mechanism 97 engages the drive screw 90.

The catheter assembly is attached to the motor drive unit 22, i.e., with the clamping collar 69 attached to the main body casing 42 through the sterile bag 31 and the motor drive-catheter interface 67 connected to the drive-shaft 64. If longitudinal translation of the transducer 36 is desired during the image scanning procedure, the pullback arm 54 is attached at one end to the pullback carriage 48 and at the other to the clamping collar 86 attached to the outer guide sheath 28.

The attending physician can then insert the outer guide sheath 28 through a hemostasis valve 136 in the patient's body and position the outer guide sheath 28 and the transducer 36 within the vessel of the patient to be examined using standard fluoroscopic techniques and/or the techniques, such as those disclosed and described in U.S. Pat. No. 5,115,814, which is incorporated herein by reference. As is well-known in the art, the distal end of the outer guide sheath 28 should be positioned such that the entire portion of the vessel of interest can be effectively image scanned without requiring its relocation.

With the catheter 24 and the motor drive unit 22 in place, the physician may conduct an imaging scan of the patient's vessel by operating the start switch 108 to cause the high-speed rotation of the drive-shaft 64 and, correspondingly, the drive-cable 34 and transducer 36. Notably, if the physician desires only to provide a data sample associated with a single transverse section of a patient's vessel, prior to operating the start switch 106, he or she should slide the engagement tab 56 toward the main body casing 42 to disengage the engagement mechanism 97 from the drive screw 90.

Alternatively, the physician may elect to perform an automated ultrasonic imaging scan by operating the imaging system 20 in the automated longitudinal translation mode. In such a situation, the transducer 36 will be shifted longitudinally at a constant rate simultaneously with the high-speed rotation of the transducer 36. Data samples representing longitudinally spaced-apart 360° "slices" of the patient's interior vessel walls can thereby be accumulated, which can be reconstructed using known algorithms and displayed in two- or three-dimensional formats on the console monitor (part of 26, not shown).

Prior to any longitudinal translation of the transducer 36 relative to the outer guide sheath 28, the transducer 36 is preferably positioned at the most distal portion of the vessel to be scanned, since the imaging system 20 will produce a "distal-to-proximal" scan of the patient's vessel. Once the outer guide sheath 28 and the transducer 36 have been positioned in a region of the patent's vessel in which the physician desires to observe, the motor drive unit 22 is positioned to remove any unnecessary slack in the guide sheath 28.

In order to facilitate the automated longitudinal translation process, the base plate 118 may be attached to the pullback carriage 48 (i.e., through the sterile plastic bag 31) in order to support the motor drive unit 22, e.g., on a support structure such as a table, or on the patient's leg. As noted briefly above, the transducer 36 is most preferably translated in a distal-to-proximal direction by means of the motor drive unit 22 (i.e., in the direction of arrow 126 in FIGS. 5 and 6).

In FIG. 5, the motor drive unit 22 is shown in a position at the beginning of an automated ultrasonic imaging scan, it being noted that the pointer 122 on the pullback carriage 48 registers with the "0" marking on the scale 120. Prior to operating the starting switch 108, the physician must slide the engagement tab 56 away from the main body casing 42 to engage the engagement mechanism 97 to the drive screw 90. The physician will then initiate the automated ultrasonic imaging scan by operating the start switch 108, which causes the main body casing 42 to longitudinally and proximally move relative to the pullback carriage 48 (i.e., in the direction of arrow 128 in FIGS. 5 and 6). As the proximal face of the pullback carriage 48 moves away from start indicator 114, the actuator button 116 is released, thereby causing a signal to be sent to the console controller 26 indicating that the automated ultrasonic imaging scan has been initiated. Alternately, the physician could start the motor switch 108 first, and then, by sliding the engagement tab 56 away from the main body casing 42, the pullback process is started.

With the motor drive unit 22 supported on the base plate 118, the pullback carriage 48 and, thus, the pullback arm 54 will remain "fixed," regardless of the longitudinal movement of the main body casing 42. As such, the outer guide sheath 28 will remain fixed by the pullback arm 54. A proximal longitudinal movement of the main body casing 42 will result in a corresponding proximal longitudinal movement of the respective drive-cable 34 and telescoping inner sheath 38 relative to the outer guide sheath 28. Consequently, the transducer 36 will proximally and longitudinally move from its most distal position (indicated by a vertical axis line 124) a distance equal to that moved by the main body casing 42 relative to the pullback carriage 48, as registered by the pointer 122 on the scale 120.

In FIG. 7, the motor drive unit 22 is shown in a position at the end of an automated ultrasonic imaging scan, it being noted that the pointer 122 on the pullback carriage 48 now registers with the "10" marking on the scale 120.

Rather than supporting the motor drive unit 22 on the base plate 118, the physician may instead elect to hold the main body casing 42 of the motor drive unit 22 in his or her hand. In this instance, while keeping the portion of the outer guide sheath 28 between the clamping collar 86 and the hemostasis valve 136 sufficiently straight, the physician may initiate the automated ultrasonic imaging scan with the same effect as described above by manually moving the main body casing 42 longitudinally and proximally at approximately the same rate as that which the pullback carriage 48 travels relative to the main body casing 42. This "matching of speeds" can be facilitated by maintaining a uniform tension in the outer guide sheath 28 between the clamping collar 86 and hemostasis valve 136, while moving the main body casing 42.

Referring to FIG. 8, the physician can alternately prevent the main body casing 42 of the motor drive unit 22 from moving proximally during the automated ultrasonic imaging scan. In particular, with the main body casing 42 in a fixed position, the pullback carriage 48 and, thus, the pullback arm 54, longitudinally and distally move in the direction of arrow 130. As a result, the distance between the clamping collar 86 and the hemostasis valve 136 decreases. Since the outer guide sheath 28 is anchored by the clamping collar 86 and the hemostasis valve 136, the outer guide sheath 28 is laterally deflected or "bowed." Such lateral deflection of the outer guide sheath 28 causes the telescoping inner sheath 38 and, thus, the drive-cable 34, to longitudinally move in the direction of arrow 132, i.e., from its most distal position a distance equal to that moved by the main body casing 42 relative to the pullback carriage 48, as registered by the pointer 122 on the scale 120.

In this later situation, as the main body casing 42 reaches its most proximal position relative to the pullback carriage 48, the mechanical disengage member 112 contacts and disengages the engagement mechanism 97 from the drive screw 90, terminating the automated ultrasonic imaging process. Upon the main body casing 42 reaching its most proximal position relative to the pullback carriage, the pointer 122 on the pullback carriage registers with the marking "10" on the scale 120. Of course, the automated ultrasonic imaging procedure need not necessarily be conducted over the entire range of "0–10" marked on the scale 120 (i.e., the fullest possible range of movement of the main body casing 42 relative to the pullback carriage 48), but instead could be terminated at any time, i.e., by sliding the engagement tab 56 toward the main body casing 42 to disengage the engagement mechanism 97 from the drive screw 90.

In certain instances, a physician may wish to provide data samples associated with discrete and different transverse sections of the patient's vessel, without necessarily accumulating the data from multiple, equally spaced slices. For instance, it may be desirable to analyze discrete images of selected areas of the patient's vessel. In such a case, the physician can operate the imaging system 20 in a manual longitudinal translation mode by sliding the engagement tab 56 toward the main body casing 42 to disengage the engagement mechanism 97 from and the drive screw 90. The physician can then manually move the main body casing 42 relative to the pullback carriage 48 to place the rotating transducer 36 in the desired portion of the patient's vessel to be imaged. The exact relative position of the transducer 36 can be determined by referring to the position indicated by the pointer 122 on the scale 120.

Those skilled in this art will recognize that a number of alternative mechanical and/or electrical means could be employed in the afore-described preferred embodiments. For example, rather than the drive screw 90 and engagement mechanism 97 assembly, a drive gear and rack assembly, or a drive belt assembly may be employed to longitudinally translate the main body casing 42 relative to the pullback carriage 48. Examples of these alternatives are disclosed and described in co-pending U.S. patent applications Ser. No. 08/722,325, entitled "Device for Controlled Longitudinal Movement of an Operative element Within a Catheter Sheath and Method" and U.S. Ser. No. 08/721,433, entitled "Catheter System and Drive Assembly Thereof," which are each fully incorporated herein by reference.

Also, rather than the engagement tab 57 and ball detent mechanism 59, locking slides, latches or quarter-turn screws could be used to allow engagement and disengagement of the threaded end 96 of the engagement mechanism 97 to and from the drive screw 90.

Still further, as opposed to the power/data cable 25, power could be supplied by batteries and data/instructions could be transmitted using radio frequency transmitters and receivers so as to make the motor drive unit 22 entirely self-contained.

Further still, various automated longitudinal translation rates may be selected for various purposes. For example, slow rates give ample time for the physician to examine the real-time images in cases where time is not a limiting factor. The upper rate limit is governed by the transducer 36 rotation rate and the effective thickness of the imaging data slices generated by the probe, such that there is an acceptable gap between successive imaging data vectors and slices. This would prevent missing discernible features or vector overwriting during vascular imaging during automated translation of the transducer 36. The effective thickness is governed by the beam characteristics of the transducer 36. For some applications, the longitudinal translation of the transducer 36 may be discontinuous (i.e., gated to an electrocardiogram) for use with modified algorithms or programmed to translate a fixed distance discontinuously.

Moreover, while particularly adapted for imaging of vascular regions using a transducer 36, the disclosed embodiment of the invention could be modified to provide controlled longitudinal movement of other rotating operative elements such as rotating arthrectomy devices. Furthermore, the invention is not limited for use in vascular regions, but can be also used in other bodily cavities and passages.

Thus, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A motor drive assembly, comprising:
   a main body adapted for attachment to a catheter assembly;
   a motor means housed in, and secured to, the main body;
   a drive shaft means for rotating an operative element disposed in the catheter assembly, the drive shaft means having a first end rotationally coupled to the motor means and a second end adapted for rotationally coupling to the operative element;
   a pullback carriage means for slidingly engaging the main body;
   a drive train means rotatably attached to the main body and engagable to the pullback carriage means for causing movement of the pullback carriage means relative to the main body when the drive train means is rotated; and
   a gear means for communicating with the drive shaft means and drive train means, such that rotation of the drive shaft means causes corresponding rotation of the drive train means.

2. The motor drive assembly of claim 1, further comprising a pullback arm means attachable at one end to the pullback carriage means and at the other end to an outer sheath of the catheter assembly, such that, when the drive shaft means is coupled to the operative element, movement of the main body relative to the pullback carriage means causes coincidental movement of the operative element relative to the outer sheath.

3. The motor drive assembly of claim 1, further comprising a base plate means attachable to the pullback carriage means.

4. The motor drive assembly of claim 1, wherein the main body comprises a pair of guide rail means, and the pullback carriage means comprises a pair of collar means, each collar means for slidingly engaging a respective guide rail means.

5. The motor drive assembly of claim 1, wherein the drive train means comprises:
   a drive screw means rotatably mounted to the main body for rotational communication with the gear means, and
   a threaded collar means pivotally mounted to the pullback carriage means and engagable with the drive screw means for causing translational movement of the main body relative to the pullback carriage means.

6. The motor drive assembly of claim 5, wherein the pullback carriage means comprises a latch means for alternately engaging or disengaging the pullback carriage means to or from the threaded collar means.

7. The motor drive assembly of claim 5, further comprising a disengage means attached to the main body for disengaging the threaded collar means from the drive screw means when the main body moves to a predetermined position relative to the pullback carriage means.

8. The motor drive assembly of claim 1, wherein the gear means comprises a reduction gear means, such that rotation of the drive shaft means at a first angular velocity causes corresponding rotation of the drive train means at a second angular velocity, the second angular velocity being substantially less than the first angular velocity.

9. The motor drive assembly of claim 1, further comprising a motion indicator means attached to the main body for sending a signal to an external controller when the main body moves away from a start position relative to the pullback carriage means.

10. An imaging system, comprising:
   a) a catheter assembly comprising an outer sheath and an operative element disposed therein;
   b) a motor drive assembly means including:
      i) a main body adapted for attachment to the catheter assembly;

ii) a motor means housed in and secured to the main body;

iii) a drive shaft means for rotationally coupling the motor means to the operative element;

iv) a pullback carriage means for slidingly engaging the main body;

v) a drive train means rotatably attached to the main body and engagable to the pullback carriage means for causing movement of the pullback carriage means relative to the main body when the drive train means is rotated; and vi) a gear means for communicating rotationally with the respective drive shaft means and drive train means, such that rotation of the drive shaft means causes corresponding rotation of the drive train means; and c) a pullback arm means for causing coincidental movement of the operative element relative to the outer sheath upon movement of the main body relative to the pullback carriage means when the drive shaft means is coupled to the operative element.

11. The imaging system of claim 10, further comprising a base plate means attachable to the pullback carriage means.

12. The imaging system of claim 10, wherein the main body comprises a pair of guide rail means, and the pullback carriage means comprises a pair of collar means, each collar means for slidingly engaging a respective guide rail means.

13. The imaging system of claim 10, wherein the drive train means comprises a drive screw means rotatably mounted to the main body for communicating rotationally with the gear means, and a threaded collar means pivotally mounted to the pullback carriage means and engagable with the drive screw means for causing translational movement of the main body relative to the pullback carriage means.

14. The imaging system of claim 13, wherein the pullback carriage means comprises a latch means for alternately engaging or disengaging the pullback carriage means to or from the threaded collar means.

15. The imaging system of claim 14, further comprising a disengage means attached to the main body for disengaging the threaded collar means from the drive screw means when the main body moves to a predetermined position relative to the pullback carriage means.

16. The imaging system of claim 10, wherein the gear means comprises a reduction gear means, such that rotation of the drive shaft means at a first angular velocity causes corresponding rotation of the drive train means at a second angular velocity, the second angular velocity being substantially less than the first angular velocity.

17. A motor drive assembly, comprising:

a main body means for attaching to a catheter assembly;

a pullback carriage means for slidingly engaging the main body means;

a motor means housed in the main body means for rotationally coupling to a drive shaft means;

a drive train means for rotationally coupling the main body means to the drive shaft means, the drive train means being engagable to the pullback carriage means for causing movement of the pullback carriage means relative to the main body means when the drive shaft means is rotated.

18. The motor drive assembly of claim 17, further comprising a gear reduction means for communicating rotationally with the respective drive shaft means and drive train means, such that rotation of the drive shaft means causes corresponding rotation of the drive train means at a substantially slower angular velocity.

* * * * *